United States Patent [19]

Backus

[11] Patent Number: 5,705,366
[45] Date of Patent: Jan. 6, 1998

[54] COAMPLIFICATION OF TARGET NUCLEIC ACIDS USING VOLUME EXCLUSION AGENT IN REACTION COMPOSITION, TEST KIT AND TEST DEVICE USEFUL THEREFOR

[75] Inventor: John W. Backus, Williamson, N.Y.

[73] Assignee: Johnson & Johnson Clinical Diagnostics, Inc., Rochester, N.Y.

[21] Appl. No.: 306,792

[22] Filed: Sep. 15, 1994

[51] Int. Cl.$^6$ .............. C12P 19/34; C12Q 1/68; C12Q 1/70; C07H 21/04

[52] U.S. Cl. .............. 435/91.2; 435/6; 435/5; 536/23.1; 536/24.3; 536/24.32; 536/24.33

[58] Field of Search .............. 435/91.2, 6, 5, 435/23.1; 536/24.3, 24.33

[56] References Cited

U.S. PATENT DOCUMENTS

| | | | |
|---|---|---|---|
| 3,798,320 | 3/1974 | Weiss et al. | 424/92 |
| 4,302,204 | 11/1981 | Wahl et al. | 23/230.3 |
| 4,683,202 | 7/1987 | Mullis et al. | 435/91 |
| 4,766,064 | 8/1988 | Williams et al. | 435/6 |
| 4,795,698 | 1/1989 | Owen et al. | 455/4 |
| 5,106,730 | 4/1992 | Van Ness et al. | 435/6 |
| 5,185,243 | 2/1993 | Ullman et al. | 435/6 |
| 5,194,370 | 3/1993 | Berninger et al. | 435/6 |
| 5,229,297 | 7/1993 | Schnipelsky et al. | 436/94 |
| 5,340,728 | 8/1994 | Grosz et al. | 435/91.2 |

FOREIGN PATENT DOCUMENTS 0 543 484 A2  5/1993  European Pat. Off. .......... C12Q 1/68

OTHER PUBLICATIONS

Udy G. et al PCR amplification of DNA from replicadated ES cells Technique, vol. 2(2):88–92, 1990.

Lehtovaara, P. et al, Quantitative PCR for Hepatitis B Virus with Coloumetric Detection, PCR methods and Applications 3:169–175, 1993.

Perkin Elmer Cetus Biotechnology Catalog, pp. 10, 60–66, 1991.

Pomp and Medrano, Organic Solvents as Facilitators of Polymerase chain reaction, Biotechnique 10(1)58–59, 1991.

Sambrook et al. In Molecular Cloning:a Laboratory Manual p. 9.50, publishers Cold Spring Harbor Lab, 1989.

Wetmur, Biopolymers 10:601–613, 1971.

Zimmerman et al. PNAS 80:5852–5865, 1983.

Wahl et al. PNAS 76:3683–3687, 1989.

*Primary Examiner*—W. Gary Jones
*Assistant Examiner*—Dianne Rees
*Attorney, Agent, or Firm*—Stasia L. Ogden

[57] ABSTRACT

Multiple target nucleic acids are amplified using polymerase chain reaction in the presence of a nonionic, polymeric volume exclusion agent. The amplification efficiency of low copy target nucleic acids is increased in the presence of the volume exclusion agent even though reduced primer levels are used. In this manner, amplification efficiency of a given target nucleic acid can be more readily manipulated.

15 Claims, No Drawings

5,705,366

COAMPLIFICATION OF TARGET NUCLEIC ACIDS USING VOLUME EXCLUSION AGENT IN REACTION COMPOSITION, TEST KIT AND TEST DEVICE USEFUL THEREFOR

FIELD OF THE INVENTION

This invention relates to a rapid method for coamplification of two or more double-stranded nucleic acids using a volume exclusion agent in the reaction mixture. It also relates to a reaction composition, test kit and test device which are useful for carrying out the method of the invention.

BACKGROUND OF THE INVENTION

Detection of nucleic acids has grown in recent years as a means for early detection of genomic features, infectious agents and various organisms which are present in very small quantities in a human or animal test specimen. Detection procedures are normally based on the concept of complementarity whereby two DNA strands are bound together by hydrogen bonds and other forces between complementary nucleotides (which are known as nucleotide pairs).

A DNA molecule is normally quite stable, but the strands can be separated or denatured by certain conditions, such as heating. The denatured strands will reassociate only with another strand having a complementary sequence of nucleotides.

Much research has been carried out to find ways to detect only a few molecules of a DNA. Various procedures are known and have been used for almost a decade to amplify or greatly multiply the number of nucleic acids in a specimen for detection. Such amplification techniques include polymerase chain reaction (PCR), ligase chain reaction (LCR) and others which are less developed.

PCR is the most well known and involves the hybridization of primers to the strands of a target nucleic acid in the presence of a DNA polymerization agent and deoxyribonucleotide triphosphates under appropriate conditions. The result is the formation of primer extension products throughout several cycles and exponential multiplication of the number of original target strands. Further details about PCR can be obtained by consulting U.S. Pat. No. 4,683,195 (Mullis et al), U.S. Pat. No. 4,683,202 (Mullis) and U.S. Pat. No. 4,965,188 (Mullis et al).

Human and animal specimens contain many different nucleic acids, some of which are endogenous (or natural) to the person or animal, and others which are produced because of some abnormal condition, such as from the presence of an infectious agent or an oncogenic condition. Such nucleic acids are usually present in very low concentrations compared to endogenous nucleic acids. They are sometimes referred to as "low copy number" nucleic acids. By comparison, the endogenous nucleic acids are usually present in high concentrations and may be referred to as "high copy number" nucleic acids. One such example is human β-globin DNA.

Frequently, in using PCR, two or more nucleic acids present in the specimen are amplified at the same time in the same reaction container. This is identified herein as "coamplification". This process requires that primers for each nucleic acid to be amplified must be simultaneously present in the container.

When both low and high copy target nucleic acids are amplified in such situations, amplification of the low copy target nucleic acid is often inhibited. This is due to the saturation of the amplifying enzyme (such as DNA polymerase) by the high copy target nucleic acid during the later cycles of amplification. False negative results for the presence of the low copy target nucleic acid are likely, with possibly serious consequences.

Various solutions to the problem have been proposed for PCR, including adjusting the concentrations of the primers, utilizing primer sets with specific melting temperatures (Tm's), or combinations thereof. Adjusting the primer ratios has been referred in the art as "primer biasing" the PCR yield, and requires a decrease in the concentration of primers for the high copy target nucleic acid. Only modest control of the process is achieved with this approach.

Another approach to coamplification has been to adjust the temperature of annealing in PCR such that the primers for the high copy target nucleic acid anneal to a lesser extent than those for the low copy target nucleic acid. This approach also has a problem. The $T_m$ difference between primer pairs must be relatively large before good modulation of PCR can be exerted on the differential yields for the high and low copy nucleic acids. Exact $T_m$'s cannot be calculated (although they can be estimated), and thus they must be measured. This requires a high degree of effort, and considerable tedium.

All of these approaches to modulate coamplification require that the high and low copy target nucleic acid sequences be known.

Alternatively, adding time to the priming or extension steps in PCR in later cycles can minimize the DNA polymerase saturation by the high copy target nucleic acid and increase amplification efficiency. However, this solution has limited utility in situations where many nucleic acids which are present in varying concentrations, are being amplified simultaneously.

It is known that the hybridization rate of nucleic acids is increased considerably in the presence of volume exclusion agents such as dextran sulfate or polyethylene glycol due to exclusion of nucleic acids from the volume of solution occupied by the agents [Sambrook et al, *Molecular Cloning, A Laboratory Manual*, page 9.50, 1989, and U.S. Pat. No. 5,106,730 (Van Ness et al)]. This exclusion effect increases the effective concentration of the nucleic acids in the solution, thereby increasing the rate of hybridization. Thus, such materials are routinely added to reaction mixtures to "drive" unfavorable reactions forward. For example, they are added to reaction mixtures to "drive" ligase reactions, U.S. Pat. No. 5,185,243 (Ullman et al) and U.S. Pat. No. 5,194,370 (Berninger et al).

However, while hybridization rates are increased with volume exclusion agents, their use is not recommended by Sambrook et al unless the rate of hybridization is normally slow, or the nucleic acid is rate limiting in the reaction. Otherwise, it is known that the agents sometimes lead to high backgrounds, and the resulting solutions are more difficult to handle due to higher viscosity. Thus, the art would suggest that volume exclusion agents be limited to certain hybridization conditions, and as the patents noted above show, in practice they are used only in instances where unfavored reactions are to be "driven" forward because they would not otherwise occur at reasonable rates.

It would be desirable to achieve rapid and efficient amplification of one or more target nucleic acids when coamplified in the presence of one or more other target nucleic acids in a manner which overcomes the problems noted above.

SUMMARY OF THE INVENTION

The problems noted above are overcome with a method for the coamplification of two or more target nucleic acids, the method comprising at least 15 primary amplification cycles, each primary amplification cycle comprising the sequential steps of:

A) heating a reaction mixture of two or more target nucleic acids, or their primer extension products, at a first temperature, $T_1$, for denaturation of the strands of the target nucleic acids or their primer extension products, B) priming the denatured strands with a set of primers specific to and hybridizable with opposing strands of each target nucleic acid to be amplified, by cooling to a second temperature, $T_2$, and C) either as a continuation of step B) or in a separate step, forming primer extension products in a reaction mixture of PCR reagents, by incubation at a third temperature, $T_3$, provided that when priming and primer extension product formation are carried out in the same step, $T_2$ and $T_3$ are the same, wherein the reaction mixture in at least one of the primary amplification cycles comprises at least about 4 weight % of a nonionic, polymeric volume exclusion agent.

This invention also provides a method for the coamplification of two or more target nucleic acids and detection of one of more of the target nucleic acids, the method comprising at least 15 primary amplification cycles, each primary amplification cycle comprising the sequential steps of:

A) heating a reaction mixture of two or more target nucleic acids, or their primer extension products, at a first temperature, $T_1$, for denaturation of the strands of the target nucleic acids or their primer extension products, B) priming the denatured strands with a set of primers specific to and hybridizable with opposing strands of each target nucleic acid to be amplified, by cooling to a second temperature, $T_2$, C) either as a continuation of step B) or in a separate step, forming primer extension products in a reaction mixture of PCR reagents, by incubation at a third temperature, $T_3$, provided that when priming and primer extension product formation are carried out in the same step, $T_2$ and $T_3$ are the same, wherein the reaction mixture in at least one of the primary amplification cycles comprises at least about 4 weight % of a nonionic, polymeric volume exclusion agent, and D) after the last primary amplification cycle, detecting one or more of the primer extension products as an indication of one of more of the target nucleic acids.

Moreover, an amplification reaction composition which is buffered to a pH of from about 7.5 to about 9, comprises:
one or more sets of primers,
a thermostable DNA polymerase,
a plurality of dNTP's, and
at least about 4 weight % of a nonionic, polymeric volume exclusion agent.

A test kit of this invention comprises, individually packaged:

a) an amplification reaction composition buffered to a pH of from about 7.5 to about 9 and comprising:
one or more sets of primers,
a thermostable DNA polymerase,
a plurality of dNTP's, and
at least about 4 weight % of a nonionic, polymeric volume exclusion agent, and b) a capture reagent comprising an oligonucleotide immobilized on a water-insoluble substrate.

Still further, a self-contained test device comprises, in separate compartments:

a) an amplification reaction composition buffered to a pH of from about 7.5 to about 9 and comprising:
one or more sets of primers,
a thermostable DNA polymerase,
a plurality of dNTP's, and
at least about 4 weight % of a nonionic, polymeric volume exclusion agent, and b) a capture reagent comprising an oligonucleotide immobilized on a water-insoluble substrate, the compartments being connected in the test device so that the amplification reaction composition can be brought into contact with the capture reagent after amplification without opening the test device.

The present invention provides a very rapid and efficient method for preferentially amplifying a nucleic acid in a mixture of one or more other nucleic acids which are being coamplified. For example, the invention can be used to preferentially amplify and detect a low copy target nucleic acid over amplified high copy target nucleic acids. In such instances, the inhibition of low copy target nucleic acid amplification by the high copy target nucleic acid, is reduced. In other instances, the invention can be used to manipulate the amplification of one target nucleic acid over the others for various reasons.

The advantages of this invention are achieved by including a water-soluble or water-swellable, nonionic, polymeric volume exclusion agent within the amplification reaction mixture in at least one amplification cycle. The presence of this agent effectively allows the user to reduce the amount of primer needed for efficient amplification of the nucleic acids, which reduction then allows manipulation of the procedure so one nucleic acid is amplified preferentially. Thus, the primer can then be used as a rate limiting reactant.

In addition, the volume exclusion agent also increases the rate of renaturation of the amplification reaction products which further reduces amplification efficiency for high copy target nucleic acids compared to the low copy target nucleic acids.

In preferred embodiments, the concentration of each primer used in the amplification is quite low compared to the conventional levels. This low level is possible because of the presence of the volume exclusion agent, and it allows manipulation of the coamplification of multiple target nucleic acids even further.

In view of the teaching of the art, notably, Sambrook et al, one would not use volume exclusion agents in amplification methods because the hybridization rates are quite fast in those methods and the target nucleic acids are not present in rate limiting amounts. Moreover, one would expect that the agents would "drive" all unfavorable reactions and create considerable unwanted product. This does not appear to be the case with the present invention. The advantages provided by the present invention, then, were not expected.

The amplification procedures of this invention are carried out under what are known as "high stringency" conditions, meaning that primers hybridize specifically to the target nucleic acid strands of interest under stringent temperature, pH and other reaction conditions in a relatively rapid manner.

DETAILED DESCRIPTION OF THE INVENTION

The general principles and conditions for amplification and detection of nucleic acids using polymerase chain reaction are quite well known, the details of which are provided in numerous references including U.S. Pat. No. 4,683,195, U.S. Pat. No. 4,683,202 and U.S. Pat. No. 4,965,188 (noted above), all of which are incorporated herein by reference. Thus, in view of the teaching in the art and the specific teaching provided herein, a worker skilled in the art should have no difficulty in practicing the present invention by making the adjustments taught herein to coamplify two or more nucleic acids, one of which is preferably a low copy target nucleic acid.

The present invention is preferably directed to the amplification and detection of one or more specific nucleic acid sequences present in one or more low copy target nucleic acids in a test specimen simultaneously with the amplification of one or more nucleic acid sequences present in one or more high copy target nucleic acids. Generally, a low copy target nucleic acid is present in a specimen in an amount of less than about $10^{-16}$ molar, however, the amount can be greater if the high copy nucleic acids are present in much higher amounts, for example, at least 1000 times greater in concentration. High copy target nucleic acids are those generally associated with single copy genes while low copy target nucleic acids are generally those associated with infectious agents, cancers and other pathological conditions in a human or animal.

In addition, the high copy target nucleic acid can be used as a "positive control" in an assay. By modulating the efficiency of PCR of the high copy target nucleic acid, the positive control can be detectable only if PCR was carried out efficiently, thereby reducing the probability of false negatives. In such instances, the high copy target nucleic acid may be present at 10 or more times the concentration of the low copy target nucleic acid.

Test specimens can include cellular or viral material, hair, body fluids or other materials containing genetic DNA or RNA which can be detected. Target nucleic acids can be obtained from various sources including plasmids, and naturally occurring DNA or RNA from any source (such as bacteria, yeast, viruses, plants, higher animals or humans). It may be extracted from various tissues including blood, peripheral blood mononuclear cells (PBMC), other tissue materials or other sources known in the art using known procedures. The present invention is particularly useful for the coamplification and detection of nucleic acid sequences found in genomic DNA, bacterial DNA, proviral DNA, fungal DNA, viral RNA, or DNA or RNA found in bacterial or viral infected cells. In addition, nucleic acid sequences associated with cancer markers are amplifiable and detectable using the present invention.

Bacteria which can be detected include, but are not limited to, bacteria found in human blood, *Salmonella spp., Chlamydia spp., Neisseria spp., Shigella spp.* and *Mycobacterium spp*. Viruses which are detectable include, but are not limited to, herpes simplex viruses, Epstein Barr virus, human cytomegalovirus, human papilloma virus, hepatitis viruses and retroviruses such as HTLV-I, HTLV-II, HIV1 and HIV2. Protozoan parasites, yeasts and molds are also detectable. Other detectable species would be readily apparent to one skilled in the art. The invention is particularly useful for the detection of the presence of DNA associated with a retroviral DNA (HIV1 or HIV2) or a Mycobacterium species. Most preferably, it is used to detect DNA associated with HIV1, proviral HIV1, HIV2 or proviral HIV2.

A "PCR reagent" refers to any of the reagents generally used in PCR, namely a set of primers for the opposing strands of each target nucleic acid, a DNA polymerase, a DNA polymerase cofactor, and two or more deoxyribonucleoside-5'-triphosphates (dNTP's).

The term "primer" refers to an oligonucleotide, whether naturally occurring or synthetically produced, which is capable of acting as a point of initiation of synthesis when placed under conditions in which synthesis of a primer extension product complementary to a nucleic acid strand (that is, template) is induced. Such conditions include the presence of the other PCR reagents, and suitable temperature and pH. Normally, such conditions are what are known in the art as "high stringency" conditions so that nonspecific amplification is minimized. The primer must be long enough to initiate the synthesis of extension products in the presence of the DNA polymerase. The exact size of each primer will vary depending upon the use contemplated, the complexity of the targeted sequence, reaction temperature and the source of the primer. Generally, the primers used in this invention will have from 10 to 60 nucleotides.

Primers can be obtained from a number of sources or prepared using known techniques and equipment, including for example, an ABI DNA Synthesizer (available from Applied Biosystems) or a Biosearch 8600 Series or 8800 Series Synthesizer (available from Milligen-Biosearch, Inc.) and known methods for their use (for example as described in U.S. Pat. No. 4,965,188, noted above). Naturally occurring primers isolated from biological sources are also useful (such as restriction endonuclease digests). A set of at least two primers is generally used for each target nucleic acid. Thus, a plurality of sets of primers can be used simultaneously to amplify a plurality of target nucleic acids. In addition, a set of primers can include a mixture of primers for a given target nucleic acid.

DNA polymerases are well known as enzymes which will esterify and add deoxynucleoside monophosphate molecules to the 3'-hydroxy end of the primer by a phosphodiester linkage to the primer, with synthesis being template directed. Useful DNA polymerases include for example, *E. coli* DNA polymerase I, T4 DNA polymerase, Klenow polymerase, reverse transcriptase and others known in the art.

The DNA polymerase is preferably "thermostable", meaning that it is generally stable at the high temperatures used for denaturation of DNA strands. More particularly, the thermostable DNA polymerases are not substantially inactivated at the high temperatures used in PCR. Such temperatures will vary depending upon a number of reaction conditions, including pH, salt concentration, and other conditions known in the art.

A number of thermostable DNA polymerases have been reported in the art, including those mentioned in detail in U.S. Pat. No. 4,965,188 (noted above) and U.S. Pat. No. 4,889,818 (Gelfand et al), incorporated herein by reference. Particularly useful polymerases are those obtained from various Thermus bacterial species, such as *Thermus aquaticus, Thermus filiformis, Thermus flavus* or *Thermus thermophilus*. Other useful thermostable polymerases are obtained from a variety of other microbial sources including *Thermococcus literalis, Pyrococcus furiosus, Thermotoga sp.* and those described in WO-A-89/06691 (published Jul. 27, 1989). Some useful enzymes are commercially available. A number of techniques are known for isolating naturally-occurring polymerases from organisms. Cloning and other synthetic techniques for preparing polymerases using recombinant techniques are also known from the art cited above, including the Gelfand et al patent.

A DNA polymerase cofactor refers to a nonprotein compound on which the enzyme depends for activity. A number of such materials are known in the art, including manganese and magnesium salts. Useful cofactors include, but are not limited to, manganese and magnesium chlorides, sulfates, acetates and fatty acid salts. The chlorides, sulfates and acetates are preferred, and the magnesium chlorides and sulfates are most preferred.

Also needed for PCR are two or more deoxyribonucleoside-5'-triphosphates, such as dATP, dCTP, dGTP, dTTP and dUTP. Analogues such as dITP and 7-deaza-dGTP are also useful. Preferably, the four common triphosphates (dATP, dCTP, dGTP and dTTP) are used in PCR.

Also useful in the practice of the invention is an antibody specific to the DNA polymerase, which antibody inhibits its enzymatic activity at temperatures below about 50° C., but which antibody is deactivated at higher temperatures. Representative monoclonal antibodies having these properties are described in U.S. Pat. No. 5,338,671 (by Scalice et al), incorporated herein by reference. Antibody fragments can be used in place of the whole molecule if they have equivalent properties.

A typical PCR reaction composition minimally contains one or more sets of primers for the target nucleic acids, a thermostable DNA polymerase (as defined above), a plurality of dNTP's (such as the conventional four dNTP's) and one or more water-soluble or water-swellable, nonionic, polymeric volume exclusion agents.

Moreover, they are nonionic, thereby excluding from the scope of this invention, cationic, anionic or amphoteric materials which can adversely affect PCR.

The volume exclusion agents are polymeric, meaning that they typically comprise a plurality of repeating units, and generally have an average molecular weight of from about 1000 to about 20,000 daltons, with a molecular weight in the range of from about 3000 to about 12,000 daltons being preferred.

Useful classes of materials which can be used as volume exclusion agents in the practice of this invention include, but are not limited to, polyethers, reaction products of a simple sugar (such as dextrose or glucose) with epichlorohydrin, polysaccharides, polyacrylates and similar materials readily one skit to one skilled in the art.

Polyethers are preferred. They can be generally represented by the formula:

wherein R is alkylene of 1 to 6 carbon atoms and n is an integer of 15 to 1000 (weight average basis). For example, R can be 1,2-ethylene, 1,2-propylene, 2-hydroxy-1,3-propylene, 3-hydroxy-1,2-propylene, 1,4-butylene, 1,3-butylene, 1,2-hexylene and other divalent alkylene groups which would be readily apparent to one skilled in the art. Preferably, R is 1,2-ethylene or 1,2-propylene as in poly (ethylene oxide) or poly(propylene oxide), which are commonly known as poly(ethylene glycol) and poly(propylene glycol), respectively.

In the noted formula, the integer "n" represents the weight average molecular weight of the compound divided by the monomeric unit molecular weight. For the preferred compounds noted in the preceeding paragraph, the average molecular weights are at least about 1000, preferably at least about 3000, and generally up to about 20,000. One skilled in the art can readily determine the appropriate "n" number of units for a given compound and compound weight. Generally, n is an integer of from 15 to 1000. As used in defining the molecular weights, the term "about" refers to a variance of ±10%.

Also included within the definition of polyethers are condensation products of ethylene oxide, propylene oxide or other alkylene oxides or various moieties such as diols, triols, sugars or acids, including polyglycidols. Such materials are well known in the art as nonionic surfactants or detergents and may be useful in the present invention provided the requisite water solubility or water swellability parameters are met.

Nonionic polysaccharides useful in the practice of this invention include dextran, glycogen and others readily apparent to one skilled in the art.

Examples of useful polyacrylates include, but are not limited to, poly(hydroxyethyl acrylate), poly(2,3-dihydroxypropyl acrylate) and others readily apparent to one skilled in the art.

The PCR reagents described herein are provided and used in PCR in suitable concentrations to provide amplification of the target nucleic acid. The minimal amount of DNA polymerase is generally at least about 1 unit/100 µl of solution, with from about 4 to about 25 units/100 µl being preferred. A "unit" is defined herein as the amount of enzyme activity required to incorporate 10 nmoles of total nucleotides (dNTP's) into an extending nucleic acid chain in 30 minutes at 74° C. The concentration of each primer is at least about 0.025 µmolar and less than about 1 µmolar with from about 0.05 to about 0.2 µmolar being preferred. All primers are present in about the same amount (within a variation of 10% of each). The cofactor is generally present in an amount of from about 1 to about 15 mmolar, and each dNTP is generally present at from about 0.15 to about 3.5 mmolar in the reaction mixture. The volume exclusion agent is present in an amount of at least about 4 weight percent, with amounts within the range of from about 6 to about 12 weight % being preferred. As used in defining the amounts of materials, the term "about" refers to a variation of ±10% of the indicated amount.

The PCR reagents can be supplied individually, or in a buffered solution having a pH in the range of from about 7 to about 9 using any suitable buffer. Thus, a reaction mixture for PCR can contain a set of primers for each low copy target nucleic acid, a set of primers for each high copy target nucleic acid, suitable dNTP's, a thermostable DNA polymerase, a cofactor for the DNA polymerase, one or more volume exclusion agents, and any other addenda that one skilled in the art would consider useful in the amplification or eventual detection of the target nucleic acids.

A target nucleic acid can be obtained from any of a variety of sources as noted above. Generally, it must be extracted in some manner to make it available for contact with the primers and other reaction materials. This usually means removing unwanted proteins and cellular matter from the specimen in a suitable manner. Various procedures are known in the art, including those described by Laure et al in *The Lance*, pp. 53–540 (Sep. 3, 1988), Maniatis et al, *Molecular Cloning: A Laboratory Manual*, pp. 280–281 (1982), Gross-Belland et al in *Eur. J. Biochem.*, 36, 32 (1973) and U.S. Pat. No. 4,965,188 (noted above). Extraction of DNA from whole blood or components thereof are described, for example, in EP-A-0 393 744 (published Oct. 24, 1990), Bell et al, *Proc. Natl. Acad. Sci. USA*, 78(9), pp. 5759–5763 (1981), Saiki et al, *Bio/Technology*, 3, pp. 1008–1012 (1985) and U.S. Pat. No. 5,231,015 (Cummins et al). The particular extraction procedure is not essential to the practice of the present invention.

Since the target nucleic acid to be amplified and detected is usually in double strand form, the two strands must be separated (that is, denatured) before priming can take place.

This can occur during the extraction process, but preferably, it occurs in a separate step afterwards. Heating to a suitable temperature (identified as "first temperature" or $T_1$ herein) is a preferred means for denaturation. Generally, this first temperature is in the range of from about 85° to about 100° C. for a suitable time, for example from 1 to about 240 seconds (preferably 1 to about 40 seconds). This initial denaturation step can also be included in the first amplification cycle. In such instances, denaturation may be longer in the first cycle (for example, up to 240 seconds) whereas later cycles can have much shorter denaturation steps (for example, up to 30 seconds).

The denatured strands are then primed with the appropriate sets of primers by cooling the reaction mixture to a second temperature, $T_2$, which is generally within the range of from about 55° to about 70° C. It is desired that cooling is done quickly as possible, but with presently known equipment, it generally takes place over a time period of from about 5 to about 40 seconds, and more preferably for from about 5 to about 20 seconds. Preferably, $T_2$ is defined as:

$$(T_{mH}-15)°C. \leq T_2 \leq (T_{mH}+5)°C.$$

wherein $T_{mH}$ is the melting temperature of the primers for the high copy target nucleic acid.

Once the denatured strands are cooled, the reaction mixture containing the PCR reagents is incubated at a third temperature, $T_3$, generally for from 1 to about 120 seconds, and preferably for from 1 to about 80 seconds, to effect formation of primer extension products. Generally, the third temperature is defined as:

$$(T_{mH}15)°C. \leq T_3 \leq (T_{mH}+15)°C.$$

and is generally within the range of from about 55° to about 70° C. Preferably, it is within the range of from about 62° to about 70° C.

In a most preferred embodiment, the second and third temperatures are the same and are within the range of from about 62° to about 70° C. Thus, priming and primer extension are preferably carried out in the same step.

Each primer for the high copy target nucleic acid also has a melting temperature identified herein as $T_{mH}$. Usually, the difference between $T_{mL}$ and $T_{mH}$ is from 0° to about 8° C., and both $T_2$ and $T_3$ are usually lower than $T_{mL}$ or $T_{mH}$ or equal to either $T_{mL}$ or $T_{mH}$. $T_{mL}$ is the melting temperature of the primers for the low copy target nucleic acid.

Melting temperature is defined herein as the temperature at which one-half of a primer is denatured from a complementary strand (such as the template). The determination of the melting temperatures can be accomplished using several standard procedures, based on ultraviolet hypochromism, for example, by monitoring the spectrum at 260 nm as described in Biochemistry-The Molecular Basis of Cell Structure and Function, 2d Edition, Lehninger, Worth Publishers, Inc., 1970, pp. 876–7. The various methods of determining melting temperatures may produce slightly differing values for the same DNA molecule, but those values should not vary by more than about 2° or 3° C. Moreover, the difference between $T_{mL}$ and $T_{mH}$ should not vary within a given method for determining melting temperatures.

Preferably, the melting temperatures are calculated using the formula:

$$T_m(°C.)=67.5+0.34(\%G+C.)-395/N$$

wherein "G" and "C" represent the number of guanine and cytosine nucleotides, respectively, and "N" represents the total number of nucleotides in the oligonucleotide (that is, the primer). Melting temperature values obtained by this calculation correlate very well with the values determined empirically at room temperature using conventional UV hypochromism and a conventional Hewlett-Packard diode array spectrophotometer (scanning rate of about +1° C./min.) for a solution of primer in 10 mmolar tris (hydroxymethyl)aminomethane buffer (pH 8.5) having an ionic strength of at least about 20 mmolar provided by one or more inorganic or organic salts, such as magnesium chloride, sodium chloride and others readily apparent to one skilled in the art. The amounts of primer and its complement in the solution used to determine the noted melting temperature formula were sufficient to provide an optical density of from about 0.5 to about 1.0 OD units.

Thus, a "primary" amplification cycle comprises the denaturation, priming (or annealing) and primer extension steps described above. Generally, at least 15 of such primary amplification cycles are carried out in the practice of this invention with the maximum number of cycles being within the discretion of the particular user. In most instances, 15 to 50 primary amplification cycles are used in the method with 15 to 40 cycles being preferred. Each primary amplification cycle is generally from about 20 to about 360 seconds, with a cycle time of from about 30 to about 120 seconds being preferred and from about 30 to about 90 seconds being more preferred. However, longer or shorter cycle times can be used if desired.

The method of this invention can comprise solely the noted "primary" cycles, but in another embodiment, the method can comprise at least 15 primary amplification cycles as defined above, followed by one or more "secondary" amplification cycles. Such secondary cycles are carried out using the same steps as the primary cycles, except that a renaturation step is included after each denaturation step and before the priming step.

Renaturation is accomplished by cooling the reaction mixture to a fourth temperature, $T_4$, defined as:

$$(T_{mH}+5)°C. \leq T_4 \leq T_{pH}$$

wherein $T_{PH}$ is the melting temperature of the double strands of the high copy target nucleic acid. Generally, $T_4$ is from about 65° to about 90° C. The time needed to reach $T_4$ is as short as possible, but it may be up to about 45 seconds, and that temperature can be maintained for from about 15 to about 100 seconds.

At least 5 secondary amplification cycles are used in the method with an upper limit being at the discretion of the user. Preferably, one embodiment of the method includes from 5 to 20 secondary cycles, with 15 cycles being most preferred. The time for each secondary cycle is from about 20 to about 360 seconds. A preferred cycle time is from about 30 to about 120 seconds.

Inclusion of a product renaturation step in the later cycles at a temperature at or below the effective high copy product $T_m$ (melting temperature) but several degrees above the effective $T_m$ of the primers used in the amplification reaction allows for renaturation of amplification products in a concentration dependent manner. The relatively short renaturation step of the secondary cycles does not substantially affect the efficiency of priming of the low copy target nucleic acid, but will decrease priming of the high copy target nucleic acid.

As used in this application, when used in reference to time for a given step, the term "about" refers to ±10% of that time limit. When used in reference to temperatures, the term "about" refers to ±5° C.

The kinetics of nucleic acid hybridization reactions, such as renaturation of amplification products, are linearly related to the concentration of the nucleic acids being hybridized. Therefore, as the concentration of amplified product increases for example, 10 times, the hybridization rate also increases 10 times (and the $t_{1/2}$ for renaturation decreases 10 times). Assuming a forward rate constant for hybridization of $5 \times 10^6$ molar$^{-1}$sec$^{-1}$, the $t_{1/2}$ would be about 14 seconds at a product concentration of $10^{-8}$ molar, and 140 seconds at a product concentration $10^{-9}$ molar. Inclusion of the volume exclusion agent as described herein leads to an effective increase in reacting macromolecules, such as amplification primers, target nucleic acids, primer extension products and DNA polymerase. This resulting increase in effective primer concentration allows for a corresponding reduction in absolute primer concentration in the amplification reaction without a loss in amplification efficiency. Thus, in the preferred practice of this invention, the primer concentration can be reduced considerably without loss in efficiency.

The amplification method of this invention is preferably conducted in a continuous, automated manner so that the reaction mixture is temperature cycled in a controlled manner for a desired number of times. A number of instruments have been developed for this purpose, as one of ordinary skill in the art would know. Preferably, the instrument used will also be programmable for both primary and secondary amplification cycles.

One such instrument for this purpose is described in some detail in U.S. Pat. No. 4,965,188 and EP-A-0 236,069. Generally, this instrument includes a heat conducting container for holding a number of reaction tubes containing reaction mixture, a means for heating, cooling and temperature maintenance, and a computing means to generate signals to control the amplification sequence, changes in temperature and timing.

EP-A-0 402 994 provides details of useful chemical test packs which can be processed using the instrument described in U.S. Pat. No. 5,089,233 (Devaney, Jr. et al), incorporated herein by reference. Also described therein are means for heating and cooling the test pack at repeated intervals (that is, through cycles) appropriate for the method of the present invention. Further details regarding useful PCR processing equipment can be obtained from the considerable literature in the field, and would be readily known by one skilled in the art.

Besides chemical test packs described above, the method can be carried out in other containers such as those described in more detail in U.S. Pat. No. 4,902,624 (Columbus et al), U.S. Pat. No. 5,173,260 (Zander et al) and U.S. Pat. No. 5,229,297 (Schnipelsky et al), all incorporated herein by reference, and any other suitable container which is readily apparent to one skilled in the art. Such test packs are also known as self-contained test devices which have separate compartments for various reagents used in the method of this invention. The compartments are appropriately connected so reagents and assay solutions can be brought into contact with the capture reagent at appropriate times without opening the device.

Detection of amplified products can be accomplished using any known procedure, including Southern blotting techniques, as described in U.S. Pat. No. 4,965,188 (noted above), or by use of labeled probes or primers, as is known in the art.

Alternatively to the embodiments described above, the amplified products can be detected using a labeled oligonucleotide which is complementary to one of the primer extension products. Procedures for attaching labels to oligonucleotides are well known. Useful labels include enzymes, ferritin and other magnetic particles, radioisotopes, chemiluminescent reagents (for example, luminol), biotin and various fluorogens and chromogens. Useful enzyme labels include glucose oxidase, peroxidase and alkaline phosphatase. Substrates and dye providing reagents for various labels, such as enzymes, are also known.

In a preferred embodiment, an enzyme label (such as peroxidase) is used for detection, and a suitable composition for providing a dye or light emission is used with that label. For example, particularly useful colorimetric dye providing systems are described in U.S. Pat. No. 5,024,935 (McClune et al). Detection is then achieved either using the unaided eye, or with suitable spectrophotometers or luminometers.

It is also possible that one of the primers of each primer set used in the method is labeled with a specific binding moiety. This moiety can be the same or different for various primers, and include any molecule for which there is a specific binding receptor which reacts specifically with that moiety. Examples of specific binding pairs (one of which can be the label) include, but are not limited to, streptavidin/biotin, sugar/lectin, antibody/hapten, antibody/antigen and others readily apparent to one skilled in the art. The receptor molecule is then conjugated with a suitable detectable label moiety such as an enzyme, radioisotope or others described above for oligonucleotides.

More preferably, one or both primers of each primer set are labeled with biotin (or an equivalent derivative thereof), and the amplified product is detected using a conjugate of streptavidin and an enzyme, such as horseradish peroxidase.

In heterogeneous detection systems of this invention, the amplified products are captured on a water-insoluble substrate of some kind, and the other materials in the reaction mixture are removed in a suitable manner, such as by filtration, centrifugation, washing or another separation technique.

Capture probes can be attached to water-insoluble supports using known attachment techniques (including absorption and covalent reactions). One such technique is described in EP-A-0 439 222 (published Sep. 18, 1991). Other techniques are described, for example, in U.S. Pat. No. 4,713,326 (Dattagupta et al), U.S. Pat. No. 4,914,210 (Levenson et al) and EP-B-0 070 687 (published Jan. 26, 1983). Useful separation means include filtration through membranes such as polyamide microporous membranes commercially available from Pall Corporation.

However, any useful solid support can be used to anchor the capture probe and eventual hybridization product, including microtiter plates, test tubes, beakers, magnetic or polymeric particles, metals, ceramics, and glass wool to name a few. Particularly useful materials are magnetic or polymeric particles having reactive groups useful for covalently attaching the capture probe. Such particles are generally from about 0.001 to about 10 μmeters. Further details about examples of such materials are provided in U.S. Pat. No. 4,997,772 (Sutton et al), U.S. Pat. No. 5,147,777 (Sutton et al), U.S. Pat. No. 5,155,166 (Danielson et al) and U.S. Pat. No. 4,795,698 (Owen et al), all incorporated herein by reference.

The capture probe can be affixed to a flat support such as a polymeric film, membranes, filter papers, or resin-coated or uncoated paper. Capture probe affixed to polymeric particles can also be immobilized on such flat supports in a suitable manner, for example, as dried deposits, or adhered by heat fusion or with adhesives. The capture probe can be affixed, for example, to a flat support in the self-contained test device of this invention. Other details of such materials are provided in EP-A-0 408 738 (published Jan. 23, 1991), WO 92/16659 (published Oct. 1, 1992) and U.S. Pat. No. 5,173,260 (Sutton et al).

The capture probes can be arranged on a suitable support in any configuration, for example rows of round deposits or stripes.

The present invention can also be used in what are known as "homogeneous" amplification procedures in which multiple target nucleic acids are simultaneously detected without the need for capture reagents. The details of such assays are known in the art, such as EP-A-0 487 218 (published May 27, 1992) and EP-A-0 512 334 (published Nov. 11, 1992).

The amplification reaction composition of this invention can be included as one individually packaged component of a test kit useful for various amplification assays. The kit can include other reagents, solutions, equipment and instructions useful in the method of this invention, including capture reagents immobilized on a water-insoluble substrate, wash solutions, extraction solutions, detection reagents and other materials readily apparent to one skilled in the art.

The following examples are included to illustrate the practice of this invention, and are not meant to be limiting in any way. All percentages are by weight unless otherwise noted.

MATERIALS AND METHODS FOR EXAMPLES

The primers used in the Examples had the following sequences. The first two are complementary to the gag region of proviral HIV1 DNA, and the second two primers are complementary to human β-globin DNA.
SEQ ID NO:1: 5'-X-ATAATCCACC TATCCCAGTA GGAGAAAT-3'
SEQ ID NO:2: 5'-X-TTTGGTCCTT GTCTTATGTC CAGAATGC-3'
SEQ ID NO:3: 5'-X-CAACTTCATC CACGTTCACC-3'
SEQ ID NO:4: 5'-ACACAACTGT GTTCACTAGC-3'

In the primers, X represents a biotinyl moiety (derived from a biotin phosphoramidite reagent, DuPont) appended to the oligonucleotide through two aminotetraethylene glycol spacer groups using the technology described in U.S. Pat. No. 4,962,029 (Levenson et al).

The capture probes used in the Examples had the following sequences, the first being for proviral HIV1 DNA and the second for human β-globin DNA:
SEQ ID NO:5: 5'-ATCCTGGGAT TAAATAAAAT AGTAAGAATG TATAGCCCTA C-Y-3'
SEQ ID NO:6: 5'-CCTCAAACAG ACACCATGGT GCACCTGACT C-Y-3'

"Y" represents two tetraethylene glycol spacers connected to a single aminediol linking group using the teaching of U.S. Pat. No. 4,914,210 (Levenson et al).

The primers and capture probes were prepared using known starting materials and procedures using an Applied Biosystems Model 380B, three column DNA synthesizer, standard phosphoramidite chemistry and the ABI 1 μmolar scale, fast cycle protocol. Nucleoside-3'-phosphoramidites and nucleoside derivatized controlled pore glass supports were obtained from Applied Biosystems. All purifications were carried out using a nucleic acid purification column, followed by reversed phase HPLC techniques.

To form capture reagents, the probes were covalently attached to polymeric particles(1 μm average diameter) prepared, using conventional emulsion polymerization techniques, from poly[styrene-co-3-(p-vinylbenzylthio) propionic acid](95:5 weight ratio, 1 μm average diameter).

A suspension of the particles in water was washed with 2-(N-morpholino)ethanesulfonic acid buffer (0.1 molar, pH 6), and suspended to about 10% solids. A sample (3.3 ml) of the washed particles, diluted to 3.33% solids in the buffer (0.1 molar, was mixed with 1-(3-dimethylaminopropyl)-3-ethylcarbodiimide hydrochloride (2.1 ml of 84 mg/ml water) and the probe (983 μl of 44.44 OD/ml nanopure water). The resulting suspension was heated at 50° C. in a water bath for about two hours with intermittent mixing and centrifuged. The particles were then washed three times with tris (hydroxymethyl)aminomethane buffer (0.01 molar, pH 8) containing (ethylenedi-nitrilo)tetraacetic acid disodium salt (0.0001 molar) and resuspended therein to 4% solids.

Upon dilution to 0.25% solids with buffer, the capture reagents (1.2 μl) were applied to and dried in defined regions of the microporous membranes (LOPRODYNE™ polyamide membrane, 5 μm average pore size, from Pall Corp.) in the test wells of SURECELL™ disposable test devices (available from Eastman Kodak Company), which are described in detail in U.S. Pat. No. 4,948,561 (Hinckley et al).

PCR was carried out using an automated Kodak PCR processor which is described in detail in U.S. Pat. No. 5,089,233,incorporated herein by reference, using the heating and cooling protocol described in the Examples below.

Recombinant DNA polymerase from *Thermus aquaticus* was obtained using conventional procedures.

Glycerol, tris(hydroxymethyl)aminomethane buffer and the dNTP's were obtained from Sigma Chemical.

Low copy target proviral HIV1 DNA was extracted from the 8E5/LAV cell line using conventional procedures. Following cell lysis and protein digestion, the DNA was purified by phenol/chloroform extraction: tris-saturated phenol (750 μl) was added to the cell suspension, and phenol/lysate solutions were mixed and separated by centrifugation. The aqueous phase was then transferred into a fresh 2 ml tube. This procedure was repeated using chloroform isoamyl alcohol. The aqueous layer was brought to 0.3 molar sodium acetate. Nucleic acids were precipitated by adding 95% cold ethanol and storing at −70° C. for 1 hour. The concentration of proviral HIV1 DNA was then determined at $A_{260}$ and serial dilutions of varying copy number were made in TE buffer [tris(hydroxymethyl)-aminomethane (1 mmolar) and (ethylenedinitrilo)-tetraacetic acid (0.1 mmolar)]for experimental use.

The high copy human β-globin DNA was obtained in human placental DNA (0.5 mg/ml) which is assumed to have two copies of the human β-globin gene per cell.

The leuco dye dispersion contained agarose (0.5%), 4,5-bis(4-dimethylaminophenyl)-2-(4-hydroxy-3-methoxyphenyl)imidazole leuco dye (250 μmolar), diethylenetriaminepentaacetic acid (100 μmolar), 4'-hydroxyacetanilide (5 mmolar), polyvinylpyrrolidone (112 mmolar) and sodium phosphate, monobasic, 1-hydrate (10 molar).

The conjugate solution used in the Examples contained a conjugate (126 μl) of streptavidin and horseradish peroxidase obtained from commercial sources (Zymed Laboratories, Inc.), casein (0.5%) and merthiolate (0.5%) in phosphate buffered saline solution (24 mmolar sodium phosphate and 75 mmolar sodium chloride). The final conjugate concentration was 312 ng/ml.

The wash solution used in the Examples contained sodium chloride (373 mmolar), (ethylenedinitrilo)tetraacetic acid disodium salt (2.5 mmolar), decyl sodium sulfate (38 mmolar) and ethylmercurithiosalicylic acid, sodium salt (25 μmolar) in sodium phosphate, monobasic 1-hydrate buffer (25 mmolar, pH 7.4).

The "TP4" monoclonal antibody was used in the reaction mixture. This antibody is specific to DNA polymerase from *Thermus aquaticus* and is described in more detail in U.S. Pat. No. 5,338,671 (noted above).

For Examples 1–4, the polymerase chain reaction mixture (200 μl) contained tris(hydroxymethyl)aminomethane buffer (10 mmolar, pH 8), potassium chloride (50 mmolar), magnesium chloride (10 mmolar), dATP, dCTP, dGTP and dTTP (1.5 molar of each), primers (either 0.1 or 0.4 μmolar of each), gelatin (0.01%), the noted DNA polymerase (8 units/200 μl), the "TP4" monoclonal antibody (50:1 molar ratio to DNA polymerase), and indicated amounts of PEG-8000 as a volume exclusion agent.

For Example 5 below, the PCR reaction mixture was the same except that only primers having SEQ ID NO:1 and SEQ ID NO:2 were used, the amount of each primer was 0.2 molar, and the amount of DNA polymerase was 32 units/200 μl.

PEG-8000, a poly(ethylene glycol) was obtained from Sigma Chemical. It has a molecular weight of about 8000 daltons.

Dextran sulfate was obtained from 5 Prime>3 Prime, Inc.

The remainder of the reagents and materials were obtained using commercial sources or prepared at Eastman Kodak Company using conventional procedures.

EXAMPLES 1–4

High Stringency Coamplification of Proviral HIV1 and β-Globin DNA Using Volume Exclusion Agent These examples demonstrate the practice of this invention using several different amplification protocols to amplify and detect a low copy target nucleic acid, proviral HIV1 DNA, in the presence of a high copy target nucleic acid, human β-globin DNA, under high stringency conditions.

The PCR reaction mixture (200 μl) described above contained 10 copies of proviral HIV1 DNA, and about 1 million copies of human β-globin DNA, and primers (either 0.1 or 0.4 μmolar of each of the four primers). Control reaction mixtures contained no volume exclusion agents while the mixtures used in the practice of this invention contained 10% of PEG-8000. The control A–D assays followed the PCR protocols of Examples 1–4, respectively.

In Example 1, the PCR protocol included 40 primary amplification cycles, each cycle of:

1) heating at 95° C. for 15 seconds for denaturation (195 seconds in the first cycle only), and 2) priming (annealing) and extension at 64° C. for 30 seconds.

The protocol of Example 2 was similar to Example 1 except priming and extension in each cycle were carried out for 60 seconds.

In Example 3, the PCR protocol included:

I) 20 primary amplification cycles, each cycle of:
  A) heating at 95° C. for 15 seconds for denaturation (195 seconds on first cycle only), and
  B) priming (annealing) and extension at 64° C. for 30 seconds, and II) 20 secondary amplification cycles, each cycle of:
  A) heating at 95° C. for 15 seconds, and
  B) priming (annealing) and extension at 64° C. for 60 seconds.

In Example 4, the PCR protocol included:

I) 20 primary amplification cycles, each cycle of:
  A) heating at 95° C. for 15 seconds for denaturation (195 seconds on first cycle only), and
  B) priming (annealing) and extension at 64° C. for 30 seconds, and II) 20 secondary amplification cycles, each cycle of:
  A) heating at 95° C. for 15 seconds,
  B) renaturation at 75° C. for 30 seconds, and
  C) priming (annealing) and extension at 64° C. for 30 seconds.

Detection of the amplification products was accomplished in the following manner. A portion (5 ml) of the final amplification reaction mixture was mixed with a buffer solution [tris(hydroxymethyl)aminomethane (10 mmolar, pH 8), potassium chloride (50 mmolar), magnesium chloride (10 mmolar) and gelatin (0.01%)] (95 ml) and incubated at 95° C. for 5 minutes to denature the nucleic acids. The resulting solution was then transferred to SURECELL™ test devices (described above) so amplified target nucleic acids could be hybridized to the capture probes at 50° C.

The test wells of the test devices were then washed at 55° C. with the noted wash solution (250 μl). The streptavidin-peroxidase conjugate solution (50 μl) noted above was then added to each test well and allowed to flow through the membrane at room temperature. After two minutes, the test wells were washed a second time.

The leuco dye dispersion (100 μl) noted above was added to each test well, and the devices were incubated at room temperature for two minutes. A solution (100 μl) of sodium azide (0.1%) was added to stop dye development. The resulting dye signals observed in the assays were visually graded on a color density scale of 0 to 10 (highest density).

The results of the assays for various primer levels, with and without PEG-8000, are shown below in Table I. It is clear that, in the presence of reduced amount of DNA polymerase, the presence of the volume exclusion agent increased the efficiency of amplification. This result is particularly evident where 0.1 μmolar of each primer was used in Examples 2 and 3, although signal increase was seen with each PCR protocol.

TABLE I

| Assay | Primer Level (μ molar) | Dye Signal |
| --- | --- | --- |
| Example 1 | 0.4 | 0.50 |
| Example 1 | 0.1 | 4.25 |
| Control A | 0.4 | 0.50 |
| Control A | 0.1 | 1.25 |
| Example 2 | 0.4 | 4.25 |
| Example 2 | 0.1 | 7.50 |
| Control B | 0.4 | 1.50 |
| Control B | 0.1 | 6.25 |
| Example 3 | 0.4 | 4.50 |
| Example 3 | 0.1 | 8.00 |
| Control C | 0.4 | 5.00 |
| Control C | 0.1 | 3.75 |
| Example 4 | 0.4 | 4.50 |
| Example 4 | 0.1 | 6.50 |
| Control D | 0.4 | 2.50 |
| Control D | 0.1 | 0 |

EXAMPLE 5

Comparison of PEG with Dextran Sulfate

This example compares the use of PEG-8000 with dextran sulfate as volume exclusion agents PCR to amplify and detect a low copy target nucleic acid, proviral HIV1 DNA. While coamplification was not carried out, this experiment demonstrates that dextran sulfate cannot be used as a volume exclusion agent in PCR. The use of PEG in coamplification has been demonstrated in Examples 1–4.

The PCR reaction mixture (200 μl) described above contained 12 copies of proviral HIV1 DNA, and about 1 million copies of human placental DNA (as background), and primers (0.2 μmolar of each). Control reaction mixtures contained no PEG-8000 or dextran sulfate while other mixtures contained 1 to 10% of PEG-8000 or dextran sulfate.

The PCR protocol included 40 primary amplification cycles, each cycle of:

1) heating at 95° C. for 15 seconds for denaturation (195 seconds in the first cycle only), and 2) priming (annealing) and extension at 64° C. for 30 seconds.

Detection of the amplification products was accomplished in the following manner. A portion (5 ml) of the final amplification reaction mixture was mixed with a buffer solution [tris(hydroxymethyl)aminomethane (10 mmolar, pH 8), potassium chloride (50 mmolar), magnesium chloride (10 mmolar) and gelatin (0.01%)] (95 ml) and incubated at 95° C. for 5 minutes to denature the nucleic acids. The resulting solution was then transferred to SURECELL™ test devices (described above) so amplified target nucleic acids could be hybridized to the capture probes at 50° C.

The test wells of the test devices were then washed at 55° C. with the noted wash solution (250 μl). The streptavidin-peroxidase conjugate solution (50 μl) noted above was then added to each test well and allowed to flow through the membrane at room temperature. After two minutes, the test wells were washed a second time.

The leuco dye dispersion (100 μl) noted above was added to each test well, and the devices were incubated at room temperature for two minutes. A solution (100 μl) of sodium azide (0.1%) was added to stop dye development. The resulting dye signals observed in the assays were visually graded on a color density scale of 0 to 10 (highest density).

The results of the assays, with and without PEG-8000 or dextran sulfate, are shown below in Table II. It is clear that, the presence of PEG-8000 increased the efficiency of amplification, while the presence of dextran sulfate totally inhibits PCR.

TABLE II

| Volume Exclusion Agent | Dye Signal |
|---|---|
| None | 4.5 |
| 1% PEG-8000 | 6 |
| 2% PEG-8000 | 7.5 |
| 4% PEG-8000 | 8.5 |
| 6% PEG-8000 | 9 |
| 8% PEG-8000 | 8.5 |
| 10% PEG-8000 | 8.5 |
| None | 6.5 |
| 1% Dextran Sulfate | 0 |
| 2% Dextran Sulfate | 0 |
| 4% Dextran Sulfate | 0 |
| 6% Dextran Sulfate | 0 |
| 8% Dextran Sulfate | 0 |
| 10% Dextran Sulfate | 0 |

The invention has been described in detail with particular reference to preferred embodiments thereof, but it will be understood that variations and modifications can be effected within the spirit and scope of the invention.

I claim:

1. A method for the coamplification of two or more target nucleic acids having different sequence compositions said method comprising at least 15 primary amplification cycles, each primary amplification cycle comprising the sequential steps of:

A) heating a reaction mixture of two or more target nucleic acids, or their primer extension products, at a first temperature, $T_1$, for denaturation of the strands of said target nucleic acids or their primer extension products, B) priming said denatured strands with a set of primers specific to and hybridizable with opposing strands of each target nucleic acid to be amplified, by cooling to a second temperature, $T_2$, and C) either as a continuation of step B) or in a separate step, forming primer extension products in a reaction mixture of PCR reagents, by incubation at a third temperature, $T_3$, provided that when priming and primer extension product formation are carried out in the same step, $T_2$ and $T_3$ are the same, wherein said reaction mixture in at least one of said primary amplification cycles comprises at least about 4 weight % of a nonionic, polymeric volume exclusion agent.

2. The method of claim 1 wherein said volume exclusion agent is selected from the group consisting of a polyether, a reaction product of a sugar with epichlorohydrin, a polysaccharide, and a polyacrylate.

3. The method of claim 2 wherein said volume exclusion agent is a polyether having the formula:

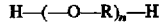

wherein R is alkylene of 1 to 6 carbon atoms and n is an integer of 15 to 1000.

4. The method of claim 3 wherein said volume exclusion agent is poly(ethylene glycol) or poly(propylene glycol).

5. The method of claim 1 wherein said volume exclusion agent has an average molecular weight of from about 1000 to about 20,000 daltons.

6. The method of claim 1 wherein said volume exclusion agent is present in said reaction mixture in an amount of from about 4 to about 12 weight %.

7. The method of claim 1 wherein at least one target nucleic acid is a low copy target nucleic acid, and at least one target nucleic acid is a high copy target nucleic acid which is suspected of being present at least about 1000 times the concentration of said low copy target nucleic acid.

8. The method of claim 1 wherein each primer of each set of primers for the target nucleic acids to be amplified is present in the same concentration which is at least about 0.025 and less than about 1 µmolar.

9. The method of claim 8 wherein each primer of each set of primers is present in a concentration of from about 0.05 to about 0.2 µmolar.

10. The method of claim 7 further comprising at least 5 secondary amplification cycles, each secondary cycle comprising repeating steps A) through C) sequentially, and additionally, between steps A) and B) of each secondary amplification cycle, the reaction mixture is cooled to and maintained at a fourth temperature, $T_4$, which is defined as:

$$(T_{mH}+5)°C. \leq T_4 \leq T_{pH}$$

wherein $T_{mH}$ is the melting temperature of the primers for said high copy target nucleic acid, and $T_{pH}$ is the melting temperature of the double strands of said high copy target nucleic acid, for from about 15 to about 120 seconds.

11. The method of claim 1 wherein steps B) and C) are the same for all cycles and $T_2$ and $T_3$ are the same temperature of from about 62° to about 70° C.

12. The method of claim 1 wherein one or both primers specific for at least one target nucleic acid are biotinylated, and detection of said amplified target nucleic acid is carried out by capturing the resulting amplified biotinylated strand using an insolubilized oligonucleotide complementary thereto, and detecting said captured biotinylated strand with a detectably labeled streptavidin conjugate.

13. The method of claim 12 wherein said oligonucleotide is immobilized on a magnetic or polymeric particle.

14. The method of claim 1 wherein each primary amplification cycle is carried out within from about 30 to about 120 seconds.

15. A method for the coamplification of two or more target nucleic acids and detection of one or more of said target nucleic acids, said method comprising at least 15 primary amplification cycles, each primary amplification cycle comprising the sequential steps of:

A) heating a reaction mixture of two or more target nucleic acids, or their primer extension products, at a first temperature, $T_1$, for denaturation of the strands of said target nucleic acids or their primer extension products, B) priming said denatured strands with a set of primers specific to and hybridizable with opposing strands of each target nucleic acid to be amplified, by cooling to a second temperature, $T_2$, C) either as a continuation of step B) or in a separate step, forming primer extension products in a reaction mixture of PCR reagents, by incubation at a third temperature, $T_3$, provided that when priming and primer extension product formation are carried out in the same step, $T_2$ and $T_3$ are the same, wherein said reaction mixture in at least one of said primary amplification cycles comprises at least about 4 weight % of a nonionic, polymeric volume exclusion agent, and D) after the last primary amplification cycle, detecting one or more of said primer extension products as an indication of one of more of said target nucleic acids.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 28
        ( B ) TYPE: Nucleic Acid
        ( C ) STRANDEDNESS: Single
        ( D ) TOPOLOGY: Linear ( i i ) MOLECULE TYPE:Primer for HIV-I DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: US-A-5,147,777

( x i ) SEQUENCE DESCRIPTION: SEQ ID NO: 1:

ATAATCCACC TATCCCAGTA GGAGAAAT    28

( 2 ) INFORMATION FOR SEQ ID NO:2:

( i ) SEQUENCE CHARACTERISTICS:
        ( A ) LENGTH: 28
        ( B ) TYPE: Nucleic acid
        ( C ) STRANDEDNESS: Single
        ( D ) TOPOLOGY: Linear ( i i ) MOLECULE TYPE: Primer for HIV-I DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: US-A-5,147,777

( x i ) SEQUENCE DESCRIPTION: SEQ ID NO: 2:

TTTGGTCCTT GTCTTATGTC CAGAATGC        28

( 2 ) INFORMATION FOR SEQ ID NO:3:

( i ) SEQUENCE CHARACTERISTICS:
               ( A ) LENGTH: 20
               ( B ) TYPE: Nucleic acid
               ( C ) STRANDEDNESS: Single
               ( D ) TOPOLOGY: Linear ( i i ) MOLECULE TYPE: Primer for b-globin DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: US-A-5,147,777

( x i ) SEQUENCE DESCRIPTION: SEQ ID NO: 3:

CAACTTCATC CACGTTCACC        20

( 2 ) INFORMATION FOR SEQ ID NO:4:

( i ) SEQUENCE CHARACTERISTICS:
               ( A ) LENGTH: 20
               ( B ) TYPE: Nucleic acid
               ( C ) STRANDEDNESS: Single
               ( D ) TOPOLOGY: Linear ( i i ) MOLECULE TYPE: Primer for b-globin DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: US-A-5,147,777

( x i ) SEQUENCE DESCRIPTION: SEQ ID NO: 4:

ACACAACTGT GTTCACTAGC        20

( 2 ) INFORMATION FOR SEQ ID NO:5:

( i ) SEQUENCE CHARACTERISTICS:
               ( A ) LENGTH: 41
               ( B ) TYPE: Nucleic acid
               ( C ) STRANDEDNESS: Single
               ( D ) TOPOLOGY: Linear ( i i ) MOLECULE TYPE: Probe for HIV-I DNA ( i i i ) HYPOTHETICAL: No (iv) ANTI-SENSE: No (vi) ORIGINAL SOURCE: Synthetically prepared (vii) IMMEDIATE SOURCE: Same (x) PUBLICATION INFORMATION: US-A-5,147,777

(xi) SEQUENCE DESCRIPTION: SEQ ID NO: 5:

ATCCTGGGAT TAAATAAAAT AGTAAGAATG TATAGCCCTA C  41

(2) INFORMATION FOR SEQ ID NO:6:

(i) SEQUENCE CHARACTERISTICS:
(A) LENGTH: 31
(B) TYPE: Nucleic acid
(C) STRANDEDNESS: Single
(D) TOPOLOGY: Linear (ii) MOLECULE TYPE: Probe for b-globin DNA (iii) HYPOTHETICAL: No (iv) ANTI-SENSE: No (vi) ORIGINAL SOURCE: Synthetically prepared (vii) IMMEDIATE SOURCE: Same (x) PUBLICATION INFORMATION: US-A-5,147,777

(xi) SEQUENCE DESCRIPTION: SEQ ID NO: 6:

CCTCAAACAG ACACCATGGT GCACCTGACT C  31